US012606794B1

(12) United States Patent
Al-Nadabi

(10) Patent No.: US 12,606,794 B1
(45) Date of Patent: Apr. 21, 2026

(54) MICROBIOLOGICAL CULTURE MEDIUM DERIVED FROM DATES AND SEA GRASS

(71) Applicant: SULTAN QABOOS UNIVERSITY, Al Khodh (OM)

(72) Inventor: Hamed Hamoud Abdullah Al-Nadabi, Muscat (OM)

(73) Assignee: SULTAN QABOOS UNIVERSITY, Al Khodh (OM)

( * ) Notice: Subject to any disclaimer, the term of this patent is extended or adjusted under 35 U.S.C. 154(b) by 0 days.

(21) Appl. No.: 19/219,231

(22) Filed: May 27, 2025

(51) Int. Cl.
*C12N 1/14* (2026.01)

(52) U.S. Cl.
CPC ...................................... *C12N 1/14* (2013.01)

(58) Field of Classification Search
CPC ...................................................... C12N 1/14
See application file for complete search history.

(56) References Cited

FOREIGN PATENT DOCUMENTS

| CN | 106047723 A | 10/2016 |
| CN | 109757302 B | 12/2021 |

OTHER PUBLICATIONS

Adnan, M., "Unraveling the Differences Between Seaweed and Seagrass", Marine Biology, Jan. 2024, 2(2), pp. 1-2.*

Ali et al., "Occurrence and Antibacterial Properties of Selected Phytochemicals in Selected Sea grasses: Acase of Chwaka Seagrasses, 2025, Biomedical Journal of Scientific & Technical Research", 66(1); pp. 55182-55187. DOI: 10.26717/BJSTR.2025.63.009832.*

Rini et al., "Date Palm (*Phoenix dactylifera* L.) Flour as an Alternative Culture Media for the Growth of *Escherichia coli* and *Bacillus cereus*", Jurnal Ilmiah Kedokteran Wijaya Kusuma 12 (1): 32-37, Mar. 2023.*

Dictionary term "Agar", from Meriam-Webster on-line dictionary. Retrieved from < https://www.merriam-webster.com/dictionary/agar> on Jan. 16, 2026.*

Nazari, Simin, et al. "Sonicated date syrup media preparation for microbial culture" African Journal of Biotechnology, vol. 10(3), pp. 424-432, Jan. 2011.

Al-Taweil, Hayyan, et al. "Use of date syrup as alternative carbon source for microbial cultivation" World Journal of Microbiology, vol. 2(1) pp. 022-025, Aug. 2015.

* cited by examiner

*Primary Examiner* — Suzanne M Noakes

(74) *Attorney, Agent, or Firm* — Nath, Goldberg & Meyer; Joshua B. Goldberg

(57) ABSTRACT

A culture medium including Faghour agar wherein the Faghour agar is made from Faghour powder derived from Mabsili dates and sea grass agar powder extracted from red sea grass.

11 Claims, No Drawings

MICROBIOLOGICAL CULTURE MEDIUM DERIVED FROM DATES AND SEA GRASS

BACKGROUND

1. Field

The present disclosure relates to a microbiological culture medium and more particularly to a culture medium derived from dates and sea grass.

2. Description of the Related Art

The cultivation of fungi and other microorganisms for research, industrial, and educational purposes commonly rely on Potato Dextrose Agar (PDA), a widely used culture medium. However, the traditional production of PDA presents several challenges including: (1) cost of production because PDA involves potato and dextrose as primary ingredients, which can be expensive and not locally available in certain regions of the world; and (2) dependency on imports because developing regions with limited access to industrial-grade materials often depend on expensive imported products, increasing research and operational costs.

Thus, new culture media supporting sustainable development while meeting the functional needs of microbiological and mycological communities are desired.

SUMMARY

The present subject matter relates to a microbiological culture medium including Faghour Agar. Faghour Agar may be a cost-effective alternative to traditional potato and dextrose agar. Faghour includes a date powder obtained by heating and drying date fruit. The date fruit may be from the Mabsili date cultivar (Besir stage). Faghour may replace potato and dextrose as the nutrient base in microbiological culture media. As Mabsili dates are abundant in regions such as Oman, this solution is a locally accessible and economical alternative for these parts of the world. The agar component is extracted from sea grass found along Oman's coastal regions. This leverages renewable and biodegradable resources, reducing the environmental footprint compared to traditional agar. By utilizing regionally abundant dates and sea grass, the microbiological cultural medium of the present teachings minimizes dependency on imported products for this region of the world which fosters self-reliance and encourages the use of indigenous resources. The innovation lowers barriers to access, enabling more laboratories, particularly in resource-limited settings, to afford quality culture media.

In an embodiment, the present subject matter relates to a culture medium including Faghour agar. The Faghour agar includes date fruit powder, sea grass powder, and water.

In another embodiment, the present subject matter relates to a method of making Faghour agar microbiological culture medium. The method may include mixing date fruit powder, sea grass powder, and water to obtain a mixture; heating the mixture until the date fruit powder and seaweed derived agar is fully dissolved; pouring the mixture into a dish; and cooling the mixture.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a microbiological culture medium using date agar, also referred to herein as "Faghour Agar." Faghour Agar may be a cost-effective alternative to traditional potato and dextrose agar. The culture medium may include a date fruit powder and a seaweed-derived agar. The date fruit powder or Faghour provides a date-derived nutrient base for the culture medium. The date fruit powder may be obtained by heating, e.g., boiling, dates, drying the heated dates, e.g., under sunlight, and reducing the dried dates to a powder. In an embodiment, the dates may be Mabsili dates, generally found in Oman. The Mabsili dates may be in a Besir stage. Faghour may serve as the nutrient base for the microbiological culture medium, providing essential carbohydrates, vitamins, and minerals for microbial growth. Faghour may be used instead of potato and dextrose, offering comparable nutritional properties for fungal cultivation. The agar component may be extracted from sea grass found along Oman's coastline, such as by non-limiting example, *Halodule uninervis, Halophila ovalis* seagrasses, and *Ulva australis*, providing a gelling agent that is renewable, biodegradable, and eco-friendly.

Faghour Agar (FA) may be used for culturing bacteria and/or fungi. In an embodiment, the FA may be optimized for culturing fungi, including yeasts and molds, making it suitable for mycological research and microbiological studies. The medium performs comparably to potato dextrose agar (PDA) in supporting fungal growth and morphology observation, ensuring reliable results for research and industrial applications.

In an embodiment, the present subject matter relates to a culture medium including Faghour agar. The Faghour agar can include Faghour powder derived from the Besir stage of Mabsili dates and sea grass derived agar.

In certain embodiments, the culture medium may include a mixture of water and Faghour agar. For example, the culture medium may include water, e.g., 1 liter of water, and Faghour agar, e.g., at least about 20 g, at least 20 g, or about 20 g to at least about 40 g, at least 40 g, or about 40 g of the Faghour agar. In still other embodiments, the Faghour agar may include at least about 28 g, at least 28 g, or about 28 g of Faghour powder and at least about 11 g, at least 11 g, or about 11 g of seaweed derived agar and 1 liter of water.

In another embodiment, the Faghour agar may be stored as a powder.

In other embodiments, the mixture of Faghour agar and water may be poured into a dish. The dish may be selected from the group consisting of petri dishes and culture plates.

In a further embodiment, the present subject matter relates to a method of making Faghour agar microbiological culture medium. The method may include mixing Faghour powder, seaweed derived agar, and distilled water to obtain a mixture. The method may include heating the mixture until the Faghour powder and seaweed derived agar is fully dissolved. The method may also include pouring the mixture into a dish and cooling the mixture.

In certain embodiments of the present production methods, at least about 28 g, at least 28 g, or about 28 g of Faghour powder and at least about 11 g, at least 11 g, or about 11 g of seaweed derived agar may be added to at least about 1 liter, at least 1 L, or about 1 L of water.

In an embodiment of the present production methods, the mixture may be sterilized by autoclaving for at least about 15 minutes. The mixture may be sterilized by autoclaving at about 121° C.

In an embodiment of the present production methods, the Faghour powder may be obtained from the boiled and dried Besir stage of Mabsili dates.

In another embodiment of the present production methods, the dish may be selected from the group consisting of a petri dish and a culture plate.

In a further embodiment of the present production methods, the method may further include adjusting the pH of the mixture by adding one selected from the group consisting of NaOH and phosphate buffer.

The formulation of Faghour Agar (FA) from date fruits powder and seaweed-derived agar is an innovative and eco-friendly product for the culturing of microbes. A number of innovative techniques may be employed in the method of preparing this formulation, including:

1) low-temperature drying: the date fruits may be dried under the sunlight which prevent the degradation of bioactive compounds;

2) ultrafine grinding: the dried date materials may be converted into micronized powder with high surface area and improved solubility and homogenization;

3) seaweed-derived agar: seaweed-derived agar may be extracted from red seaweeds, including by non-limiting example, *Halodule uninervis* and *Halophila ovalis* seagrasses, by boiling seaweed in water, followed by filtration, leaving the filtrate open for evaporation to allow the filtrate to be converted into a gel-like substance. In various embodiments, several other sophisticated techniques for the extraction of agar from seaweeds known in the art may be used.

In various embodiments, the FA described herein may be used in mycology research, e.g., for culturing, isolating, and studying fungal species, including their growth patterns and pathogenicity. The FA may also be used in education and laboratories and may provide a cost-effective alternative to PDA for teaching and academic research, enabling hands-on microbiological studies. In other embodiments, the FA described herein may be used in food and agricultural microbiology and may help in analyzing fungal contamination in food, grains, and soil samples, ensuring quality control in agriculture.

In still other embodiments, the FA may be used in pharmaceutical microbiology and may support the identification and testing of fungi in pharmaceutical environments. In an embodiment, antibiotics or pH indicators may be added to make the medium selective for particular fungal species or resistant strains, useful in pharmaceutical or clinical research. For example, Faghour Agar may be mixed with chloramphenicol to inhibit bacterial growth, while promoting fungal growth.

The FA may be enhanced by incorporating dyes (e.g., bromothymol blue) to visually differentiate fungal species based on colony color or metabolic by-products. Faghour Agar may also be used for mixed cultures, such as a formulation that supports both fungal and bacterial growth for use in ecological or environmental studies.

The FA may also be used in biotechnological and environmental studies and may facilitate research into fungal biodegradation, bioremediation, and ecosystem dynamics. For example, a bioactive Faghour Agar may be prepared by enriching the FA with bioactive compounds to study fungal interactions with other organisms or compounds. Examples may include variants with lignin or cellulose for research on fungal biodegradation or bioremediation. FA may also be used as an eco-monitoring medium where a formulation may be designed to test the presence of specific fungi in soil, water, or air samples, relevant for environmental monitoring.

The formulation of FA may be adjusted based on specific research or industrial needs, making it a versatile medium for diverse applications. Nutritional adjustments may be made to the FA for targeted microbes. For example, for bacterial growth nitrogenous sources can be added, e.g., peptone, yeast extract, tryptone; addition of minerals ($Mg^{2+}$, $Ca^{2+}$, $Fe^{2+}$); and addition of growth factors like vitamins (B1, B6, B12, folic acid). For fungal growth, the carbohydrate content may be increased by adding glucose, sucrose, or molasses.

Faghour may be naturally acidic due to the presence of organic acids in dates. As previously described, the pH can be adjusted by adding a pH adjuster such as NaOH or HCl. The pH should be around 6.8-7.4 for bacteria and around 5.0-6.0 for fungi.

The FA formulation may be made as selective media by incorporation of selective agents, e.g., addition of antibiotics to suppress the growth of bacteria, antifungal agents to suppress the growth of common molds; and crystal violet for the growth of gram-negative bacteria.

The FA may be customizable for industrial use. For example, addition of specific inducers and substrates may be made for enzyme assays. Substrates may serve as carbon, nitrogen, energy or micronutrient sources needed for growth, e.g. glucose, starch, sucrose, amylose, and phosphate. Inducers are substrates that can activate the expression of specific genes, e.g., lactose, amylose, and cellulose. Addition of metal ion or cofactor can increase the production of enzymes on an industrial scale.

The gel strength of FA may be customized by preparing variants with different agar-to-water ratios to adjust the gel strength for specific research or industrial needs, such as soft agar for motility assays or firmer agar for colony isolation.

Additional uses for FA may include portable kits for field use. For example, Compact kits containing pre-prepared Faghour Agar plates or powders, along with sterile tools may be prepared for sampling and cultivation in remote locations. Portable kits may enable on-site microbiological testing which may be particularly useful for environmental or agricultural researchers.

The following examples relate to various methods of manufacturing the specific formulations and application of the same, as described herein.

EXAMPLES

Example 1

Preparation of Faghour Powder

Mabsili dates were harvested from local farms and coastal regions in Oman. Faghour powder was obtained by boiling Mabsili dates (Besir stage), drying the date fruits under sunlight to prevent the degradation of bioactive compounds, and converting the dried dates into a micronized powder with high surface area and improved solubility and homogenization.

Example 2

Preparation of Seaweed Derived Agar

Sea grass was harvested from coastal regions of Oman. The agar component was extracted through washing, boiling, and filtration of the sea grass. Specifically, seaweed-derived agar was extracted from red seaweed by boiling the seaweed in water, followed by filtration. The filtrate was left uncovered or open for evaporation. After evaporation, the filtrate transformed into a gel-like substance. It should be understood that other sophisticated techniques can be used for the extraction of agar from seaweeds for more efficient and useful agar extraction.

Example 3

Preparation of Faghour Agar

The powdered Faghour Agar was mixed with distilled water in a specified ratio (e.g., 20-40 grams per liter of water). Specifically, twenty-eight grams (28 g) of Faghour powder was mixed with 11 grams of seaweed derived agar and added to 1 liter of water to provide a mixture. The mixture was heated until fully dissolved and sterilized (e.g., via autoclaving at 121° C., 15 psi for 15-20 minutes) to ensure a contamination-free medium. Post-autoclaved sterility was confirmed by incubating control plates and checking for contamination.

After sterilization, the agar was poured into Petri dishes or other culture containers under sterile conditions. Upon cooling, the medium solidified into a firm, gel-like surface which was suitable for microbial growth.

The pH of the Faghour media was adjusted to around 5.5-6.0 for optimal fungal growth by adding NaOH or phosphate buffer.

Example 3

Fungal Growth

*Alternaria alternata* as compared to PDA: The relative growth rates after 7 days was found faster in FA (100% coverage of petri dish) as compared to PDA with 70% coverage of petri dish in case of *Alternaria*. Furthermore, with FA, the growth fungal mycelium was faster and denser, and obtained high sporulation and pigmentation in different fungal genera, including *Fusarium, Aspergillus, Alternaria*, and *Pythium*. FA is relatively cost-effective, nutritionally rich for microbial growth, and eco-friendly as it can be obtained by converting agro-waste (seaweeds) into a useful product.

It is to be understood that the Faghour agar and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A culture medium, comprising Faghour agar, the Faghour agar including date fruit powder, seaweed derived agar, and water, wherein the date fruit powder is obtained from Mabsili dates.

2. The culture medium of claim 1, wherein the medium includes between about 20 g to about 40 g of the Faghour agar and about 1 liter of water.

3. The culture medium of claim 1, wherein the medium includes about 28 g of Mabsili date fruit powder and 11 g of seaweed derived agar.

4. The culture medium of claim 1, wherein the Faghour agar is stored in a dish selected from the group consisting of petri dishes and culture plates.

5. A method of making Faghour agar microbiological culture medium, the method comprising:

mixing Mabsili date powder, seaweed derived agar, and water to obtain a mixture;

heating the mixture until the Mabsili date powder and seaweed derived agar is fully dissolved;

pouring the mixture into a dish; and cooling the mixture.

6. The method of claim 5, wherein about 28 g of Mabsili date powder and about 11 g of seaweed derived agar are added to 1 liter of water to provide the mixture.

7. The method of claim 5, wherein the mixture is sterilized by autoclaving for about 15 minutes.

8. The method of claim 7, wherein the mixture is sterilized by autoclaving at about 121° C.

9. The method of claim 5, wherein the Mabsili date powder is provided by boiling Mabsili dates, drying the Mabsili dates to provide dried Mabsili dates, and grinding the dried Mabsili dates to provide a powder.

10. The method of claim 5, wherein the dish is selected from the group consisting of a petri dish and a culture plate.

11. The method of claim 5, further comprising adjusting a pH of the mixture by adding a pH adjuster selected from the group consisting of NaOH and phosphate buffer.

* * * * *